United States Patent
Westphal (10) Patent No.: US 11,077,221 B2
(45) Date of Patent: Aug. 3, 2021

(54) VOLATILE DISPENSER FOR USE IN VOLATILE DISPENSING SYSTEMS

(71) Applicant: S. C. JOHNSON & SON, INC., Racine, WI (US)

(72) Inventor: Nathan R. Westphal, Union Grove, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 659 days.

(21) Appl. No.: 15/005,651

(22) Filed: Jan. 25, 2016

(65) Prior Publication Data

US 2017/0209613 A1 Jul. 27, 2017

(51) Int. Cl.
| | |
|---|---|
| *A61L 9/12* | (2006.01) |
| *B65D 75/32* | (2006.01) |
| *A01M 29/12* | (2011.01) |
| *A61L 9/03* | (2006.01) |

(52) U.S. Cl.
CPC .............. *A61L 9/12* (2013.01); *A01M 29/12* (2013.01); *A61L 9/03* (2013.01); *B65D 75/325* (2013.01); *B65D 75/326* (2013.01); *A61L 2209/131* (2013.01); *A61L 2209/133* (2013.01)

(58) Field of Classification Search
CPC .. A01M 29/12; A01M 1/2044; A01M 1/2055; B65D 75/325; B65D 2577/2025; B65D 75/5855; A61L 9/12; A61L 9/03; A61L 2209/131; A61L 2209/133; A61L 2209/15; A61L 9/048; A61L 2209/11; Y10S 428/905; Y10S 261/88
USPC ....................................................... 239/34–60
See application file for complete search history.

(56) References Cited

U.S. PATENT DOCUMENTS

| | | | |
|---|---|---|---|
| 2,786,406 A | 3/1957 | White | |
| 2,898,649 A | 8/1959 | Murray | |
| 4,157,787 A * | 6/1979 | Schwartz | .................. A61L 9/12 |
| | | | 239/56 |
| 4,383,951 A | 5/1983 | Palson | |

(Continued)

FOREIGN PATENT DOCUMENTS

| | | |
|---|---|---|
| CN | 202173617 U | 3/2012 |
| CN | 103768638 A | 5/2014 |

(Continued)

OTHER PUBLICATIONS

International Search Report & Written Opinion, International Application No. PCT/US2017/012862, dated Jun. 26, 2017, 11 pages.

(Continued)

*Primary Examiner* — Joseph A Greenlund
*Assistant Examiner* — Juan C Barrera
(74) *Attorney, Agent, or Firm* — Quarles & Brady LLP (57) ABSTRACT

A volatile dispenser for use in a volatile dispensing system is provided. The volatile dispenser includes a blister with a surface having at least one flexible portion, a permeable membrane sealable to the surface and configured to form a sealed reservoir with the blister, and a volatile material contained within the sealed reservoir. Diffusion of the volatile material through the permeable membrane generates a pressure differential between the sealed reservoir and an ambient atmosphere to induce a movement of the at least one flexible portion to perform at least one function for the volatile dispensing system.

18 Claims, 7 Drawing Sheets

(56) References Cited

U.S. PATENT DOCUMENTS

| | | | |
|---|---|---|---|
| 4,574,181 A | 3/1986 | Spector | |
| 4,614,299 A * | 9/1986 | Van Loveren | A01M 1/2055 239/56 |
| 4,702,418 A | 10/1987 | Carter et al. | |
| 4,808,347 A | 2/1989 | Dawn | |
| 4,968,456 A | 11/1990 | Muderlak et al. | |
| 5,234,162 A | 8/1993 | Sullivan | |
| 5,342,584 A | 8/1994 | Fritz et al. | |
| 5,373,581 A | 12/1994 | Smith | |
| 5,394,506 A | 2/1995 | Stein et al. | |
| 5,439,100 A | 8/1995 | Gordon et al. | |
| 5,484,086 A | 1/1996 | Pu | |
| 5,605,308 A | 2/1997 | Quan et al. | |
| 5,788,931 A | 8/1998 | Quintana | |
| 5,833,929 A | 11/1998 | Watson et al. | |
| 5,903,710 A | 5/1999 | Wefler et al. | |
| 6,021,254 A | 2/2000 | Hunter | |
| 6,085,026 A | 7/2000 | Hammons et al. | |
| 6,085,027 A | 7/2000 | Sexton | |
| 6,090,349 A | 7/2000 | Hirano | |
| 6,095,153 A | 8/2000 | Kessler et al. | |
| 6,099,137 A | 8/2000 | McCormack et al. | |
| 6,135,431 A | 10/2000 | Muhmel et al. | |
| 6,197,263 B1 | 3/2001 | Blount | |
| 6,278,840 B1 | 8/2001 | Millan | |
| 6,285,830 B1 | 9/2001 | Millan | |
| 6,354,710 B1 | 3/2002 | Nacouzi | |
| 6,374,044 B1 | 4/2002 | Freidel | |
| 6,413,476 B1 | 7/2002 | Barnhart | |
| 6,443,434 B1 | 9/2002 | Vieira | |
| 6,446,583 B2 | 9/2002 | Prather | |
| 6,466,739 B2 | 10/2002 | Ambrosi et al. | |
| 6,580,875 B2 | 6/2003 | Rymer | |
| 6,592,828 B2 | 7/2003 | Munoz | |
| 6,644,507 B2 | 11/2003 | Borut et al. | |
| 6,661,967 B2 | 12/2003 | Levine et al. | |
| 6,782,194 B2 | 8/2004 | Schneiderbauer | |
| 6,796,340 B1 | 9/2004 | Ferris et al. | |
| 6,854,717 B2 | 2/2005 | Millan | |
| 6,859,615 B2 | 2/2005 | Yip et al. | |
| 6,862,403 B2 | 3/2005 | Pedrotti et al. | |
| 6,917,754 B2 | 7/2005 | Pedrotti et al. | |
| 6,920,282 B2 | 7/2005 | He et al. | |
| 6,931,202 B2 | 8/2005 | Pedrotti et al. | |
| 6,950,607 B2 | 9/2005 | Yip et al. | |
| 6,957,779 B2 | 10/2005 | Joshi et al. | |
| 6,996,335 B2 | 2/2006 | Zobele | |
| 7,082,259 B2 | 7/2006 | Zobele | |
| 7,141,215 B2 | 11/2006 | Guan et al. | |
| 7,188,780 B2 | 3/2007 | Martens, III | |
| 7,190,888 B2 | 3/2007 | Wolf et al. | |
| 7,209,650 B2 | 4/2007 | Caserta et al. | |
| 7,213,770 B2 * | 5/2007 | Martens, III | A01M 1/2055 206/484.1 |
| 7,341,698 B2 | 3/2008 | Pedrotti et al. | |
| 7,350,720 B2 | 4/2008 | Jaworski et al. | |
| 7,389,943 B2 | 6/2008 | Jaworski | |
| 7,441,360 B2 * | 10/2008 | Christianson | A47G 1/0616 362/276 |
| 7,462,329 B2 | 12/2008 | Weller | |
| 7,469,844 B2 | 12/2008 | Conway et al. | |
| 7,484,716 B2 | 2/2009 | Morie et al. | |
| 7,497,685 B2 | 3/2009 | Kubicek et al. | |
| 7,503,668 B2 | 3/2009 | Porchia et al. | |
| 7,534,406 B2 | 5/2009 | Takemura | |
| 7,544,331 B1 | 6/2009 | Pettaway | |
| 7,544,332 B2 | 6/2009 | De Silva et al. | |
| 7,548,684 B2 | 6/2009 | Berrido et al. | |
| 7,610,118 B2 | 10/2009 | Schramm et al. | |
| 7,651,666 B2 | 1/2010 | Adair et al. | |
| 7,824,627 B2 | 11/2010 | Michaels et al. | |
| 7,931,213 B2 | 4/2011 | Walter et al. | |
| 7,932,482 B2 | 4/2011 | Norwood et al. | |
| 7,938,338 B2 | 5/2011 | Janakat et al. | |
| 7,954,667 B2 | 6/2011 | Furner et al. | |
| 7,962,017 B2 | 6/2011 | Viera | |
| 7,980,486 B2 * | 7/2011 | Trent | A01M 1/2055 206/484.1 |
| 8,005,349 B2 | 8/2011 | Franco | |
| 8,061,562 B2 | 11/2011 | Carpenter et al. | |
| 8,062,598 B2 | 11/2011 | Bertassi et al. | |
| 8,091,734 B2 | 1/2012 | Furner et al. | |
| 8,170,405 B2 | 5/2012 | Harris | |
| 8,196,902 B1 | 6/2012 | Pystin | |
| 8,197,761 B1 | 6/2012 | Miller-Larry | |
| 8,342,363 B2 | 1/2013 | Carpenter et al. | |
| 8,342,370 B2 | 1/2013 | Ross et al. | |
| 8,371,310 B2 | 2/2013 | Brenneise | |
| 8,371,740 B2 | 2/2013 | Pestl et al. | |
| 8,412,029 B2 | 4/2013 | Browder et al. | |
| 8,463,114 B2 | 6/2013 | Fabrega | |
| 8,498,524 B2 | 7/2013 | Ruiz et al. | |
| 8,662,480 B1 | 3/2014 | Irvin | |
| 8,678,233 B2 | 3/2014 | Furner et al. | |
| 8,718,454 B2 | 5/2014 | Caserta et al. | |
| 8,740,107 B2 | 6/2014 | Marchetti et al. | |
| 8,750,694 B1 | 6/2014 | Porretta et al. | |
| 8,765,063 B1 * | 7/2014 | Mazzilli | A61L 9/12 239/53 |
| 8,783,510 B2 | 7/2014 | Reynolds et al. | |
| 8,787,739 B2 | 7/2014 | Hsiao | |
| 8,887,954 B2 | 11/2014 | Carpenter et al. | |
| 8,983,277 B2 | 3/2015 | Hsiao | |
| 8,983,278 B2 | 3/2015 | Ruiz et al. | |
| 8,983,279 B2 | 3/2015 | Adair et al. | |
| 8,999,259 B2 | 4/2015 | King et al. | |
| 9,031,392 B2 | 5/2015 | Hsiao | |
| 9,042,712 B2 | 5/2015 | Irvin et al. | |
| 9,144,621 B1 | 9/2015 | Finlay | |
| 9,259,750 B2 | 2/2016 | Johnson et al. | |
| 9,352,062 B2 | 5/2016 | Klemm et al. | |
| 9,388,994 B2 | 7/2016 | Hidaka et al. | |
| 9,393,337 B2 | 7/2016 | Gruenbacher et al. | |
| 9,399,080 B2 | 7/2016 | Irvin et al. | |
| 9,408,936 B2 | 8/2016 | Esses | |
| 9,522,208 B2 | 12/2016 | Esses | |
| 9,877,510 B2 | 1/2018 | Henry, Jr. | |
| 9,999,250 B2 | 6/2018 | Minskoff et al. | |
| 2002/0176704 A1 | 11/2002 | Roe | |
| 2003/0138241 A1 | 7/2003 | Pedrotti et al. | |
| 2003/0206834 A1 | 11/2003 | Chiao et al. | |
| 2004/0009103 A1 | 1/2004 | Westing | |
| 2004/0190883 A1 | 9/2004 | Kompara et al. | |
| 2005/0175331 A1 | 8/2005 | Tan et al. | |
| 2005/0220664 A1 | 10/2005 | Hitzler et al. | |
| 2006/0000922 A1 | 1/2006 | Martens | |
| 2006/0000923 A1 * | 1/2006 | Martens, III | A01M 1/2055 239/60 |
| 2006/0032937 A1 | 2/2006 | Caserta | |
| 2006/0193610 A1 | 8/2006 | Han | |
| 2006/0193611 A1 | 8/2006 | Ruiz Ballesteros et al. | |
| 2006/0292110 A1 | 12/2006 | Reinhardt | |
| 2007/0183924 A1 | 8/2007 | Morgan | |
| 2007/0183981 A1 | 8/2007 | Varanasi et al. | |
| 2007/0257016 A1 | 11/2007 | Jin et al. | |
| 2007/0262166 A1 * | 11/2007 | Majerowski | A01M 1/2055 239/57 |
| 2008/0095522 A1 | 4/2008 | Deflorian et al. | |
| 2008/0277495 A1 | 11/2008 | Duru | |
| 2009/0041442 A1 | 2/2009 | Rouse, Jr. | |
| 2009/0078253 A1 | 3/2009 | Bao | |
| 2009/0196587 A1 | 8/2009 | Cheung | |
| 2009/0232710 A1 | 9/2009 | Kinsey | |
| 2009/0302019 A1 | 12/2009 | Selenski et al. | |
| 2010/0010908 A1 | 1/2010 | Pasuplati et al. | |
| 2010/0059602 A1 | 3/2010 | Chiou et al. | |
| 2010/0178042 A1 | 7/2010 | Neumann et al. | |
| 2010/0193599 A1 | 8/2010 | Bulter et al. | |
| 2010/0326280 A1 | 12/2010 | Hicks | |
| 2011/0132995 A1 | 6/2011 | Perman | |
| 2011/0134628 A1 | 6/2011 | Pestl | |
| 2011/0139810 A1 | 6/2011 | Lee | |
| 2012/0000989 A1 | 1/2012 | Bordier | |
| 2012/0018529 A1 | 1/2012 | Gammon et al. | |

(56) References Cited

U.S. PATENT DOCUMENTS

| | | |
|---|---|---|
| 2012/0201523 A1 | 8/2012 | Tebe Poves et al. |
| 2012/0224995 A1 | 9/2012 | McMinn |
| 2013/0049236 A1 | 2/2013 | Garon et al. |
| 2014/0091487 A1* | 4/2014 | Belongia ............... A61L 9/122 261/146 |
| 2014/0112649 A1 | 4/2014 | Irvin et al. |
| 2014/0126892 A1 | 5/2014 | Hsiao |
| 2014/0145004 A1 | 5/2014 | Westphal |
| 2014/0193764 A1 | 7/2014 | Pizzini |
| 2014/0209698 A1 | 7/2014 | Olchovy et al. |
| 2014/0209700 A1* | 7/2014 | Olchovy ............... A61L 9/12 239/34 |
| 2014/0261408 A1 | 9/2014 | DePiano et al. |
| 2014/0377130 A1 | 12/2014 | Edwards et al. |
| 2015/0258289 A1 | 9/2015 | Henry et al. |
| 2015/0320899 A1 | 11/2015 | Soliz et al. |
| 2016/0015847 A1 | 1/2016 | Irvin et al. |
| 2016/0022855 A1 | 1/2016 | Esses |
| 2016/0022857 A1 | 1/2016 | Esses |
| 2016/0067367 A1 | 3/2016 | Jin et al. |
| 2016/0107186 A1 | 4/2016 | Chao |
| 2016/0152117 A1 | 6/2016 | Backman et al. |
| 2016/0256585 A1 | 9/2016 | Esses |
| 2016/0279278 A1 | 9/2016 | Gruenbacher et al. |
| 2016/0325605 A1 | 11/2016 | Irvin et al. |
| 2016/0331913 A1* | 11/2016 | Bourque ............... A61M 11/042 |
| 2017/0128608 A1 | 5/2017 | Hsiao |
| 2018/0064839 A1 | 3/2018 | Hsiao |
| 2018/0126022 A1 | 5/2018 | Hsiao |
| 2018/0126025 A1 | 5/2018 | Hsiao |

FOREIGN PATENT DOCUMENTS

| | | | |
|---|---|---|---|
| CN | 105188777 A | 12/2015 | |
| CN | 204951729 U | 1/2016 | |
| DE | 202013101904 U1 | 6/2013 | |
| EP | 0511853 A2 | 11/1992 | |
| EP | 1175833 A1 | 1/2002 | |
| ES | 2255422 A1 | 6/2006 | |
| JP | 01060918 U | 4/1989 | |
| JP | 04136082 U | 12/1992 | |
| JP | 2002200154 A | 7/2002 | |
| JP | 2003225293 A | 8/2003 | |
| JP | 2004524864 A | 8/2004 | |
| JP | 2004313004 A | 11/2004 | |
| JP | 2010506577 A | 3/2010 | |
| JP | 2010532170 A | 10/2010 | |
| JP | 2015531621 A | 11/2015 | |
| JP | S56020869 B | 11/2015 | |
| KR | 20040043304 A | 5/2004 | |
| WO | 1997039778 A1 | 10/1997 | |
| WO | 2003077961 A1 | 9/2003 | |
| WO | 2004028574 A1 | 4/2004 | |
| WO | 2005092399 A1 | 10/2005 | |
| WO | 2007018402 A1 | 2/2007 | |
| WO | 2007083042 A1 | 7/2007 | |
| WO | WO2007142851 A2 | 12/2007 | |
| WO | 2011020491 A1 | 2/2011 | |
| WO | 2013106982 A1 | 7/2013 | |
| WO | 2014022164 A1 | 2/2014 | |
| WO | 2014025720 A1 | 2/2014 | |
| WO | 2014055478 A1 | 4/2014 | |
| WO | 2014087173 A1 | 6/2014 | |
| WO | WO2015116934 A1 * | 8/2015 | ............ A61M 11/04 |
| WO | 2016083165 A1 | 6/2016 | |
| WO | 2016096272 A1 | 6/2016 | |
| WO | 2016155333 A1 | 10/2016 | |
| WO | 2016180663 A1 | 11/2016 | |

OTHER PUBLICATIONS

International Search Report & Written Opinion, International Application No. PCT/US2017/018130, dated Jun. 2, 2017, 16 pages.
International Search Report & Written Opinion, International Application No. PCT/US2017/012727, dated Dec. 5, 2017, 29 pages.
Grounds for Rejection issued in Chinese Application No. 201780027275.6, dated Apr. 29, 2020, 11 pages.
First Office Action from corresponding Japanese Patent Application No. 2018-538830, dated Dec. 1, 2020 (6 pages).

* cited by examiner

-PRIOR ART-

VOLATILE DISPENSER FOR USE IN VOLATILE DISPENSING SYSTEMS

CROSS REFERENCE TO RELATED APPLICATIONS

Not applicable

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present disclosure generally relates to volatile dispensing systems for releasing volatile materials into the air. More particularly, the disclosure is directed to dispensers configured to control the operation of the volatile dispensing systems in which they are used.

2. Description of the Background of the Invention

A variety of methods have been utilized to contain volatile materials, including insect control agents, fragrances, deodorizers, and the like, and permit the controlled dispensing of these materials as vapors into the ambient air. The prior art describes in detail the use of permeable membranes, as well as other manners to dispense volatile materials from a given dispenser. A variety of volatile material dispensers have been designed to be positioned in various open and closed areas, dependent upon the particular need for the dispenser. Furthermore, the prior art describes manners and devices for displaying the dispensers.

Specific to personal living spaces and professional office settings, there is a desire to make the ambient air more pleasing. Additionally, there is a desire for insect and pest control in these spaces, as well as outdoor spaces, on an ongoing basis. The prior art describes many such devices that may be employed for use in these spaces for both air freshening and insect control.

Figure 1A:
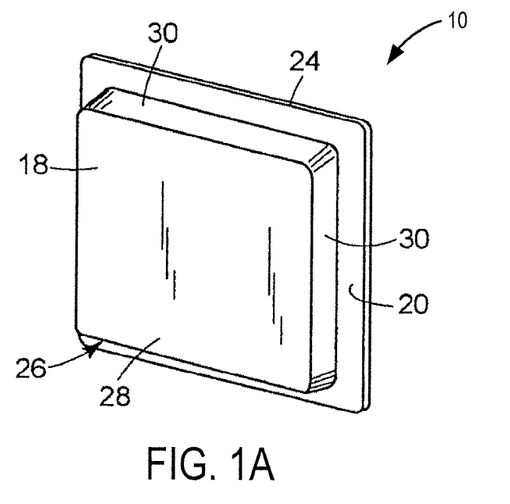
FIG. 1A is a perspective view of a prior art dispenser for use in a volatile dispensing system.
Figure 1B:
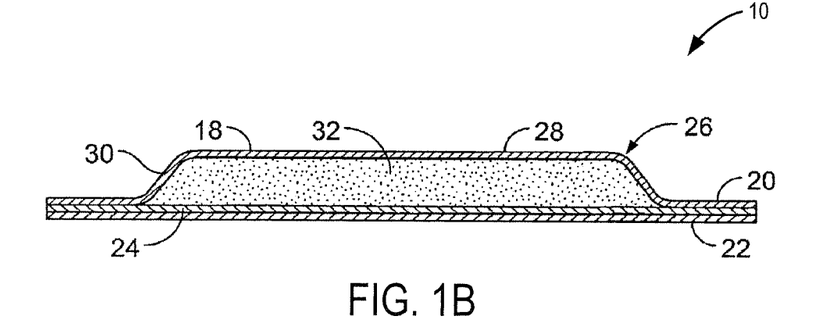
FIG. 1B is a partially enlarged sectional view of the dispenser shown in FIG. 1A.
Figure 1C:
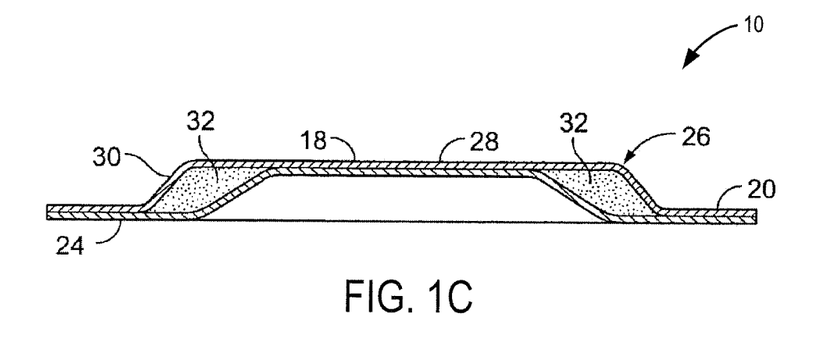
FIG. 1C is a partially enlarged sectional view of the dispenser shown in FIG. 1A after some period of use.

For instance, FIGS. 1A-1C illustrate a prior art dispenser 10 that may be used alone or in conjunction with a conventional volatile dispensing system. As shown, the dispenser 10 includes a blister 18, a flange 20, and a laminate 22 adhered to the blister 18. Typically, the blister 18 includes a permeable membrane 24, such as a semi-permeable or vapor permeable membrane, and a cup 26. In particular, the cup 26 includes a bottom wall 28 and side walls 30, that in conjunction with the membrane 24 acts as a sealed reservoir to contain the volatile material 32.

Upon removal of the laminate 22, the dispenser 10 would begin to transition from a full or first condition (FIG. 1B) toward an empty or second condition (FIG. 1C). As the volatile material 32 diffuses through the membrane 24, the membrane 24 slowly collapses upon the bottom wall 28. Specifically, with reference to FIG. 1C, following diffusion of the volatile material 32 across the membrane 24, less volatile material 32 remains within the dispenser 10. The result of this is a pressure gradient across the membrane 24, with a higher pressure existing in the ambient air compared to the pressure in the dispenser 10. The pressure gradient causes the ambient air to exert a net positive pressure upon the dispenser 10, which presses the membrane 24 against the remaining volatile material 32 and ultimately the bottom wall 28.

Continued diffusion of the volatile material 32 increases the force exerted upon the membrane 24, which causes the remaining volatile material 32 to migrate from a center of the bottom wall 28 toward a periphery of the bottom wall 28. Continued migration and diffusion of the volatile material 32 results in an increasing surface area contact between the membrane 24 and the bottom wall 28 until the dispenser 10 is empty, or nearly empty. The pressure gradient ultimately resulting in migration of the volatile material 32 may also be viewed as occurring due to an increasing compressed vacuum presence within the dispenser 10 as the volatile material 32 continues to diffuse across the membrane 24. A small amount of the volatile material 32 may remain within the dispenser 10 when it is nearly empty. The volatile material 32 will typically be present in the form of a ring-like appearance (not shown) toward the periphery of the bottom wall 28.

As may be appreciated from the above descriptions, changes in the dispenser 10, as described with reference to FIG. 1C, can have undesirable consequences with respect to the operation of a dispensing system. For instance, changes in the structure and/or dimensions of the dispenser 10 may reduce the dispensing rate and uniformity of diffusion. In addition, these changes could be exacerbated by various environmental changes, including changes in temperature or pressure.

In addition, due to the nature of the problem that is being combated, such as air treatment, freshening, or insect control, there is a societal stigma associated with the presence of such noticeable devices within the personal living spaces and professional office settings where the devices may be employed. An unsightly or clearly identified device is not desirable in such settings. Rather, it is preferable that such a device be decorative and pleasant to the user and, more importantly, to individuals who may frequent the particular settings. As such, a deformed or collapsed dispenser 10 might not only make handling and removal from a dispensing system more difficult, but could also negatively impact aesthetic appearances during operation, or more particularly during the last phases of use.

Although some dispensing products have been introduced attempting to address the above-described limitations, these have focused mainly on using heavier or thicker materials, or on including geometric features that provide stiffness to the dispenser. However, such implementations may compromise or prevent optimal product delivery, or may not achieve sufficient compensation of volumetric or dimensional changes of the dispenser. For instance, vents in the dispenser could in principle provide pressure equalization, but these might not be desirable due to the possibility of leakage or blockage. Also, including more materials or additional features to the dispenser would increase manufacturing costs.

In some dispensing systems, vents in a dispenser housing, that open and close, have been included to control volatile material output. Alternatively, or additionally, capabilities for advancing, retracting, interrupting, or adapting a heat source have also been included in various dispensing systems. Notwithstanding that such implementations would require additional complexity that would add to the cost of manufacturing, and might not necessarily address all of the above limitations, these might not be relevant to or improve some dispensing systems, such as passive dispensing systems or dispensing systems designed for a specific aesthetic appearance.

Hence, in light of the above, there is a need for improved devices that effectively and controllably dispense volatile materials.

SUMMARY OF THE INVENTION

The present disclosure overcomes the aforementioned drawbacks by providing embodiments directed to volatile material dispensing systems and dispensers. Specifically, volatile dispensers provided herein are configured to optimize volatile material delivery. As will be described, rather than compensating for structural and dimensional changes by using thicker materials or by activating or operating other dispenser system elements, such as increasing power applied to a resistor or opening a vent, embodiments described herein utilize structural and dimensional changes to directly perform various functions, such as optimizing volatile material output. That is, volatile dispenser embodiments provided herein include operational functionality that allow flexing, wrinkling, collapsing, and other movement or modification of the various dispenser surfaces affecting volatile material delivery, and performing other functions.

In accordance with one aspect of the disclosure, a volatile dispenser for use in a volatile dispensing system is provided. The volatile dispenser includes a blister with a surface having at least one flexible portion, a permeable membrane sealable to the surface and configured to form a sealed reservoir with the blister, and a volatile material contained within the sealed reservoir. Diffusion of the volatile material through the permeable membrane generates a pressure differential between the sealed reservoir and an ambient atmosphere to induce a movement of the at least one flexible portion to perform at least one function for the volatile dispensing system.

In accordance with another aspect of the disclosure, a volatile dispenser for use in a volatile dispensing system is provided. The volatile dispenser includes a blister with a surface having at least one flexible portion and at least one rigid portion adjacent to the at least one flexible portion, a permeable membrane sealable to the surface and configured to form a sealed reservoir with the blister, and a volatile material contained within the sealed reservoir. Diffusion of the volatile material through the permeable membrane generates a pressure differential between the sealed reservoir and an ambient atmosphere to induce a movement of the at least one flexible portion to perform at least one function for the volatile dispensing system.

DETAILED DESCRIPTION OF THE DRAWINGS

Figure 2A:
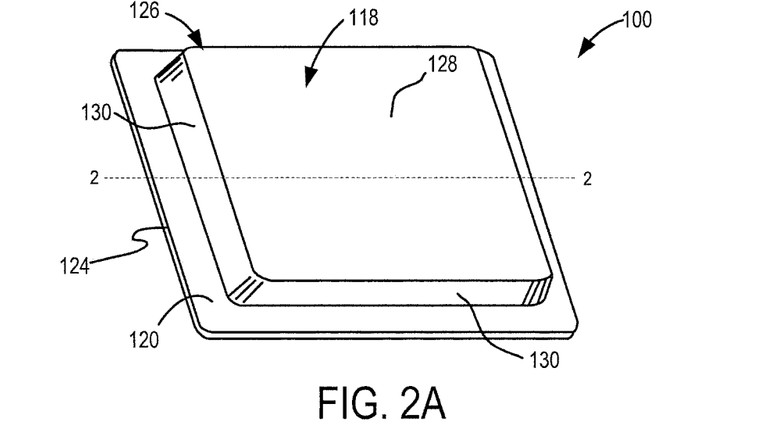
FIG. 2A is a perspective view of a volatile dispenser, in accordance with aspects of the present disclosure.
Figure 2B:
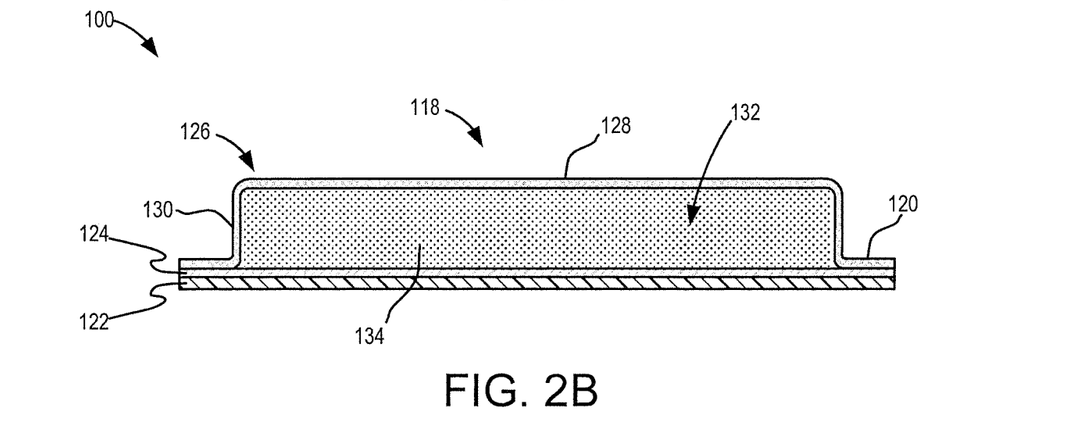
FIG. 2B is a sectional view of a volatile dispenser taken along the line 2-2 of FIG. 2A.
Figure 2C:
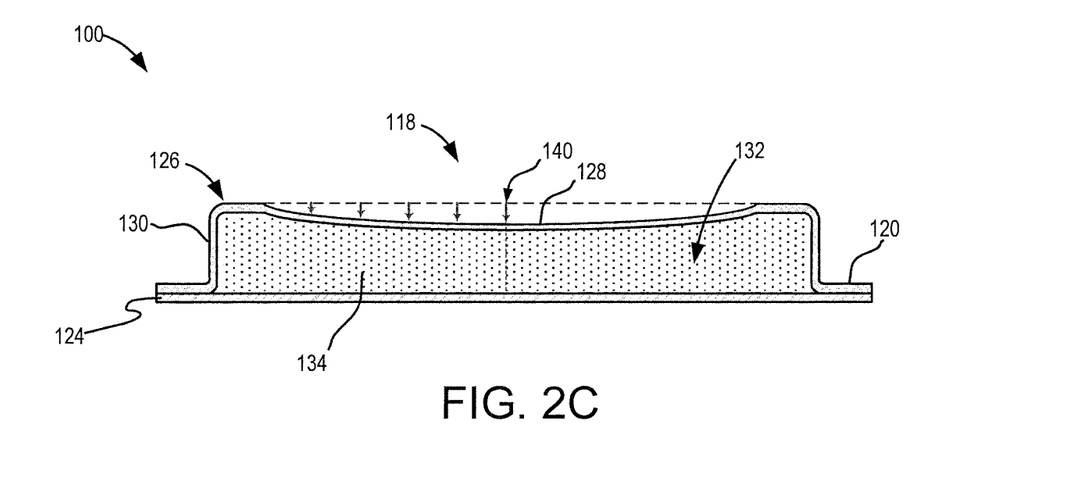
FIG. 2C is a sectional view of the volatile dispenser shown in FIG. 2B after some period of use.

With particular reference to FIGS. 2A-2C, one embodiment of a volatile dispenser 100, for use in a volatile material dispensing system, is illustrated. In general, the dispenser 100 may be characterized in the present embodiment as a cartridge having a blister 118, a peripheral flange 120, and an impermeable laminate 122 releasably adhered to the blister 118 and flange 120. The blister 118 includes a non-porous permeable membrane 124 and a cup-shaped structure 126. The cup-shaped structure 126 includes a bottom surface 128 and side walls 130 that in conjunction with the membrane 124 produce a sealed reservoir 132 to contain a volatile material 134.

The cup-shaped structure 126 may be manufactured using any materials suitable, such as polymer materials, thermoplastics and the like. In some aspects, the cup-shaped structure 126 may include a recycled polyethylene terephthalate (RPET) layer adhesively bonded to a nylon laminate. The nylon laminate may also include a layer of ethylene vinyl acetate (EVA) coextruded to each side of a middle nylon layer. The nylon laminate and RPET layer of the cup-shaped structure 126 in one embodiment have a thickness of about 0.100 to 1.500 mm, although various thicknesses may be possible. As shown in FIG. 2A, the cup-shaped structure 126 may generally be square or rectangular, with overall dimensions of up to about 3 to 5 mm high, about 50 to 60 mm long, and about 50 to 60 mm wide. In some implementations, a ratio between the surface area and height of the cup-shaped structure 126 may be approximately in a range between about 0.05:1 to 10:1, although other values may be possible. Additionally, it may be appreciated that the cup-shaped structure 126 may also be circular, oval, or any other shape having similar dimensions, depending upon the desired application.

The side walls 130 may be substantially straight, as shown in FIGS. 2A-2C, or may taper slightly outward as one moves from the bottom surface 128 to the flange 120. In alternative embodiments, the side walls 130 may taper inwardly, or comprise various angled or curvilinear surfaces. The side walls 130 of the cup-shaped structure 126 may have a height of up to about 3 to 5 mm, and a length of up to about 50 to 60 mm, although other dimensions may be possible. The bottom surface 128 may also be square or rectangular, or any other shape, with dimensions generally up to about 48 to 62 mm, although other dimensions may also be possible. In some implementations, a ratio of the surface area of the bottom surface 128 to the height of the cup-shaped structure 126 may be approximately in a range between about 0.05:1 to 10:1, although other values may be possible.

In one embodiment, the side walls 130 and bottom surface 128 of the cup-like structure 126 are thermoformed from a single sheet of the RPET and nylon laminate that is heated, then blown and/or pressed into the flange-and-cup arrangement shown in FIG. 2B. Other manufacturing or forming processes be additionally, or alternatively, carried out. In addition, the cup-shaped structure 126 may be clear or translucent, to allow for the visibility of the volatile material 132 contained within the blister 118. Alternatively, the cup-shaped structure 126 may be opaque or may include varying portions with clear, translucent, and/or opaque properties.

Figure 3A:
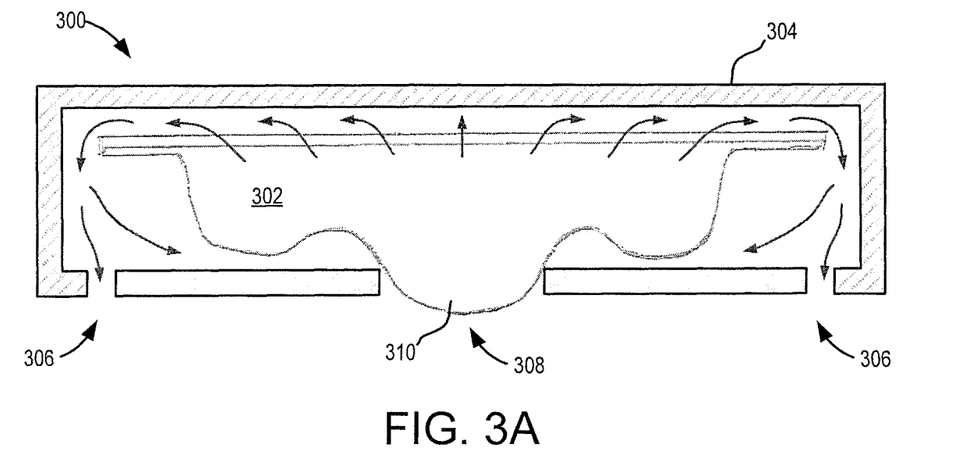
FIG. 3A is a schematic, sectional view of an example volatile dispensing system, in accordance with aspects of the present disclosure, further including a volatile dispenser similar to those shown in FIGS. 2A-2C.
Figure 3B:
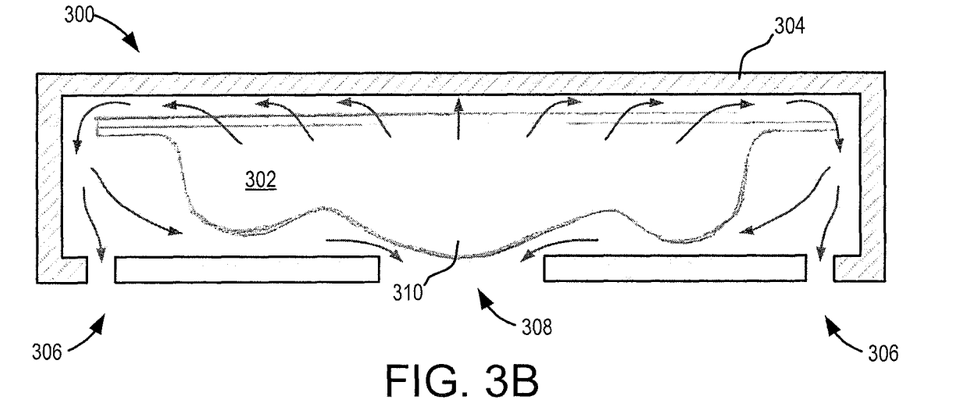
FIG. 3B is another schematic, sectional view of the example volatile dispensing system shown in FIG. 3A, following some period of use.
Figure 3C:
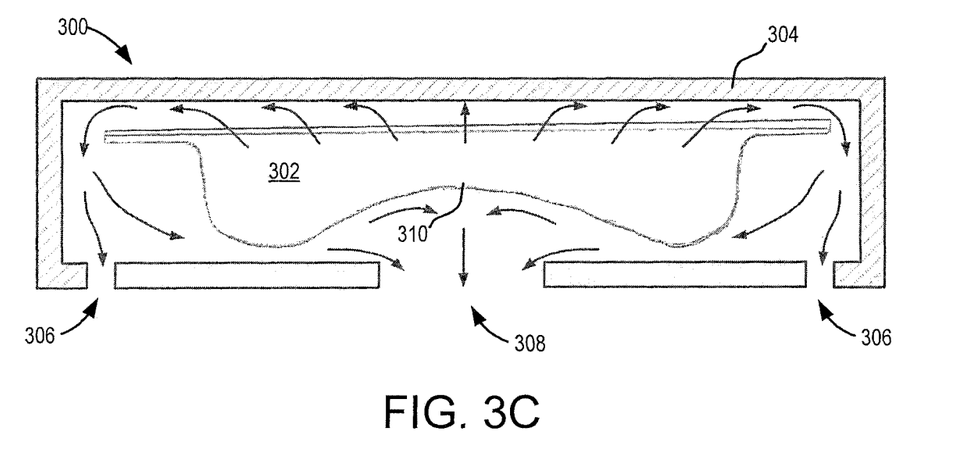
FIG. 3C is yet another schematic, sectional view of the example volatile dispensing system shown in FIG. 3B, following some additional period of use.

The cup-shaped structure 126 includes a bottom surface 128 and side walls 130, or side surfaces, as shown in FIGS. 2A-2C. However, it envisioned that various modifications are possible. For example the cup-shaped structure 126 can include fewer or more surfaces, or additional elements, and any such surfaces or elements can be flat, curved, or have any shape and dimensions, depending on the desired functionalities, for example, as illustrated in FIGS. 3A-3C. In addition, such surfaces need not be limited to a single thickness, but may indeed vary in thickness. Such implementations, for instance, would be desirable in order to control movements and functionality of various portions of the cup-shaped structure 126 substantially independently.

For instance, only a portion of the bottom surface 128 may be configured to undergo a movement as a result of a pressure differential, as shown in FIG. 2C, while other surfaces would remain substantially unchanged. Alternatively, the side walls 130 may be configured to undergo movement (not shown) while the bottom surface 128 remains substantially unchanged. In either case, this may be achieved, for example, by modifying the thickness and/or material properties in that portion or surface, relative to the rest of the cup-shaped structure 126. For instance, in order to include the properties or functionality described, such portion or surface may be modified during the forming process, or via a chemical or other subsequent treatment process.

The flange 120 may be planar, coupled to and extending outward from the top edges of the cup-shaped structure 126 (e.g. upper edges of side walls 130). In addition, the flange 120 may be integrally formed with the cup-shaped structure 126 in, for example, a thermoforming process, as described above.

As described, the membrane 124 is configured to allow diffusion of the volatile material 134 into the ambient air. Illustratively, the membrane 124 can have a thickness of about 0.05 to 0.15 mm and a density within a range of about 0.88 to 0.95 grams/cubic centimeter, although other dimensions and material properties are also possible. As an example, the membrane 124 may be comprised of low density polyethylene (LDPE). In addition, the membrane 124 may be clear to allow for visibility of the volatile material 134 contained within the blister 118. In some aspects, the membrane 124 may be preferably configured to have little or no flexure as a result of pressure differentials produced by the volatile material 134 diffusion, and/or changing ambient conditions, such as temperature or pressure.

The membrane 124 may also be formed integrally with the laminate 122 and heat fused to the flange 120 such that the membrane 124 extends across the entire cup-shaped structure 126. FIGS. 2B and 2C show the membrane 124 enclosing and sealing the cup-shaped structure 126 with the volatile material 134 stored inside, thereby forming a thin sealed container impermeable to the volatile material 134 stored therein. This container remains substantially impermeable until the user grasps a corner, end, and/or other portions of the laminate 122, and peels the laminate 122 from the membrane 124, thereby exposing the membrane 124 and permitting the volatile material 132 to migrate through the membrane 124 and diffuse into the ambient air.

The laminate 122 may include a layer of polypropylene, aluminum foil, and/or polyester. For example, polypropylene may be adhesively bonded to an aluminum foil layer, which may be adhesively bonded to a polyester layer. An extrusion bonding material may be used to bond the layers together. Illustratively, the laminate 122 may have a thickness of between 0.1 (0.004 in) and 0.2 mm (0.008 in). The polyester layer may be generally suitable for printing and may be the outer surface of the laminate 122. In some aspects, the polyester layer may be surface lacquered with a transparent nitro varnish.

Following placement of the volatile material 132 into the cup-shaped structure 126, a seal is made between the flange 120 and the permeable membrane 124, thereby forming the dispenser 100. As noted above, the laminate 122 may be attached to the blister 118 at the same time as the membrane 124 if the laminate 122 and the membrane 124 are co-extruded. The membrane 124 and the laminate 122 may be attached to the flange 120 of the blister 118 using any conventional means, such as an adhesive, heat sealing, and/or crimping, or the like. The seal is substantially airtight so as to prevent leakage of air or the volatile material 134. The volatile material 134 need not completely fill the void within the blister 118. For instance, a relatively small amount of air can be tolerated in the dispenser 100 following the creation of blister 118. For example, the air in the sealed blister is no more than about 3% to 6% of the overall volume of the blister 118. As the volatile material 134 diffuses out of dispenser 100 little or no air enters the blister 118 through the membrane 124.

The volatile material 134 can include a dispensing liquid, such as a diffusible fragrance, diffusible deodorizer, or diffusible insect control agent such as an insecticide or repellant. In some implementations, the dispensing liquid may be clear, while in others it may be dyed and may be used, for instance, to provide a user indication with respect to a state of the dispenser 100. In some aspects, the dispensing liquid may have viscous properties sufficient such that any air bubble trapped therein can quickly rise to the top of the cup-structure 126. Such properties may be desirable in applications where aesthetic appearances might be important. By way of example, a formula for the dispensing liquid can include by weight percentage about 97.4% to about 97.8% fragrance (varies by sku), about 0.100% Tween 20 (a surfactant), about 2.100% to about 2.500% Cabosil (a fumed silica), and about 0.004% to about 0.008% dye (varies by sku). Such composition would provide the dispensing liquid with a viscosity approximately between 60 and 1500 centipoise. Other envisioned volatile materials may include a gel, or other substances.

In accordance with aspects of the present disclosure, one or more portions, surfaces, or points on the side walls 130 and/or bottom surface 128 forming the cup-shaped structure 126 may be configured to move, expand, contract, flex, wrinkle, or collapse due to pressure gradients between the inside of the cup-shaped structure 126 and ambient atmosphere, as shown in the example of FIG. 2C. As described, such pressure gradients can arise during use due to the diffusion of the volatile material 134 across the membrane 124, as well as due to changes in ambient conditions, such as temperature and pressure. To this end, the thickness and/or material structure of the bottom surface 128, and/or side walls 130, either in entirety or portions thereof, may be configured to allow flexure or movement.

Figure 5A:
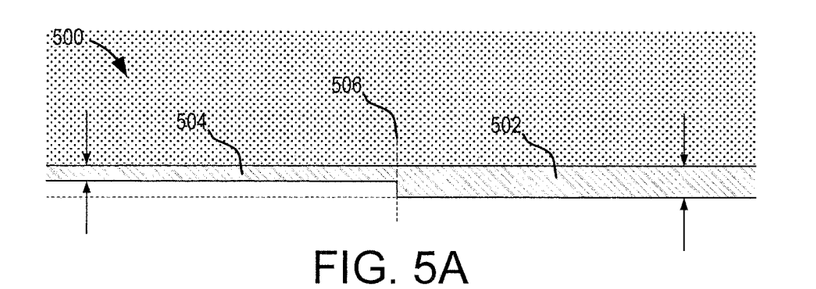
FIG. 5A is expanded view of the volatile dispenser shown in FIG. 2B showing one embodiment in accordance with the present disclosure.
Figure 5B:
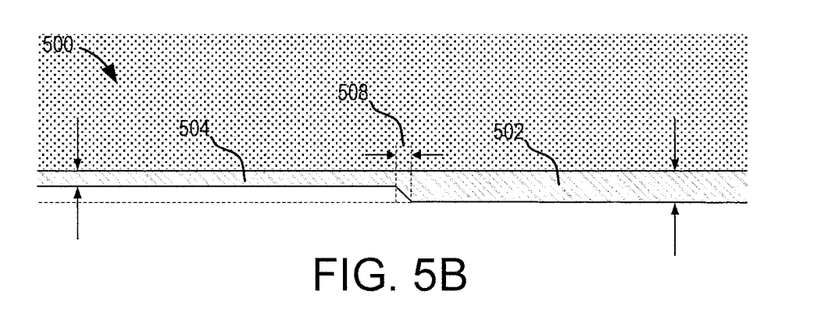
FIG. 5B is an expanded view of the volatile dispenser shown in FIG. 2B showing another embodiment in accordance with the present disclosure.
Figure 5C:
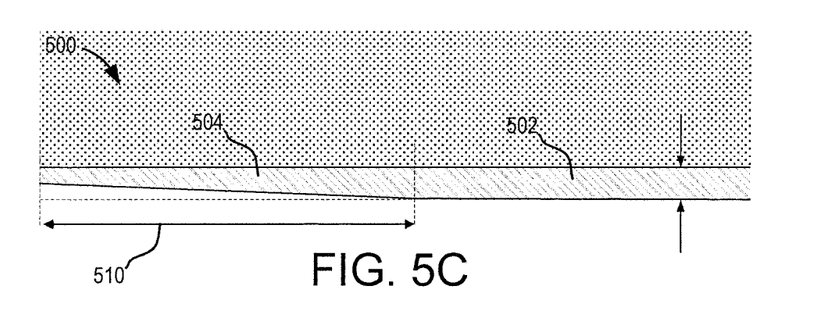
FIG. 5C is an expanded view of the volatile dispenser shown in FIG. 2B showing yet another embodiment in accordance with the present disclosure.

By way of example, FIGS. 5A-5D show an expanded view of a volatile dispenser 500, such as a section of the bottom surface 128, or side walls 130 described with respect to FIGS. 2A-2C. As shown, the section includes a rigid portion 502 adjacent to a flexible portion 504, wherein the rigid portion 502 is configured to substantially maintain its shape as a result of a pressure gradient, while the flexible portion 504 is configured to flex or move due to the pressure gradient. In particular, such flexure or movement of the flexible portion 504 can be achieved by having a thickness that is less than the rigid portion 502, as shown in FIGS. 5A-5C. For example, if the thickness of a rigid portion of the bottom surface 128 described with reference to FIG. 2B is 0.300 mm, then the thickness of the flexible portion could be 0.250 mm, 0.200 mm, or any value less than 0.300 mm. It may be readily appreciated that the structural integrity of the flexible portion 504 is required for successful operation under the operational conditions and environment of the volatile dispenser 500. With dimensionality, along with material properties, affecting structural integrity, it is envisioned that the thickness of the flexible portion 504, or various portions thereof, may be at least 20%, 30%, 40%, 50% or more of the rigid portion 502 thickness, while still being less than the thickness of the rigid portion 502.

In some aspects, the thickness between the rigid portion 502 and the flexible portion 504 can change either abruptly or gradually depending on the application and materials utilized. For instance, a thickness transition can occur over a very narrow range, such as a single point 506, as shown in FIG. 5A. Alternatively, the thickness transition can occur over a narrow range 508 or a wide range 510, as shown in FIGS. 5B and 5C, respectively. As such, the thickness transition can vary between about 0 to 33 mm, for example. Further, although the thickness transition is shown in FIGS. 5B and 5C to be monotonic and linear, it may be readily understood that such thickness transition need not be linear nor monotonic. For example, a thickness of the flexible portion 504 that extends along a given surface dimension may start at 100% of the rigid portion 502 thickness, transition to a minimum of about 20% and then return to 100%, either uniformly or non-uniformly along the surface dimension.

Figure 5D:
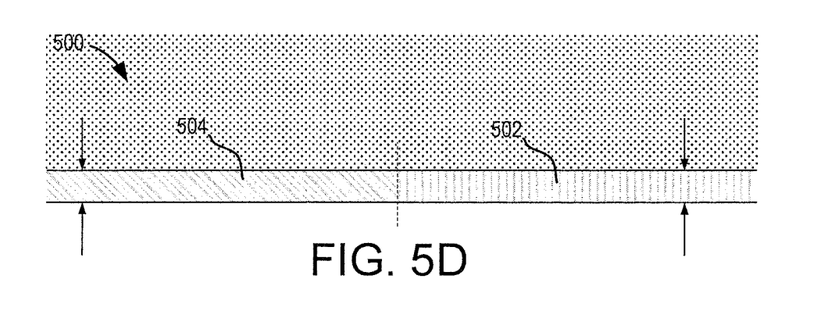
FIG. 5D is expanded view of the volatile dispenser shown in FIG. 2B showing yet another embodiment in accordance with the present disclosure.
Figure 6A:
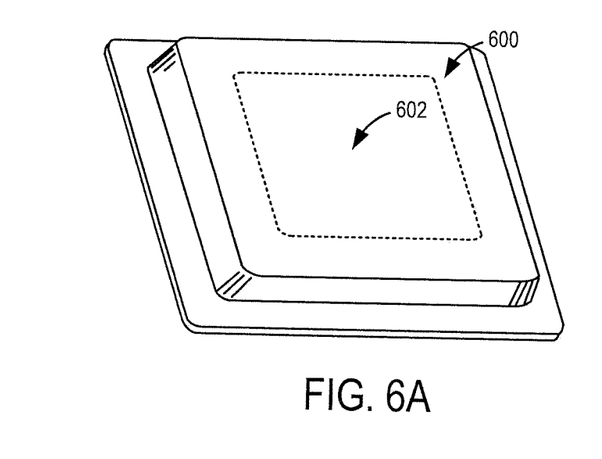
FIG. 6A is a perspective view of a volatile dispenser, in accordance with aspects of the present disclosure.
Figure 6B:
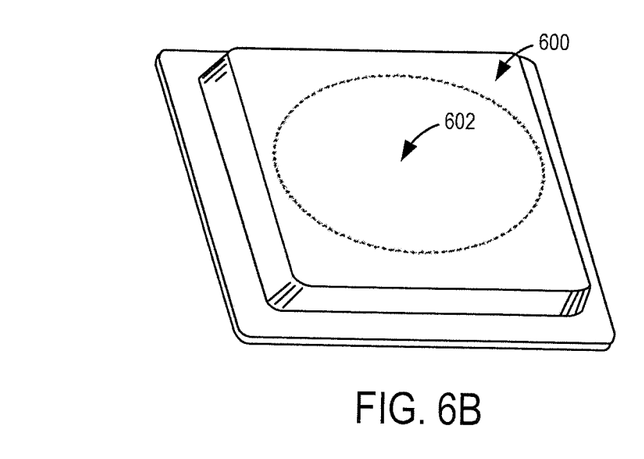
FIG. 6B is a perspective view of a volatile dispenser, in accordance with aspects of the present disclosure.
Figure 6C:
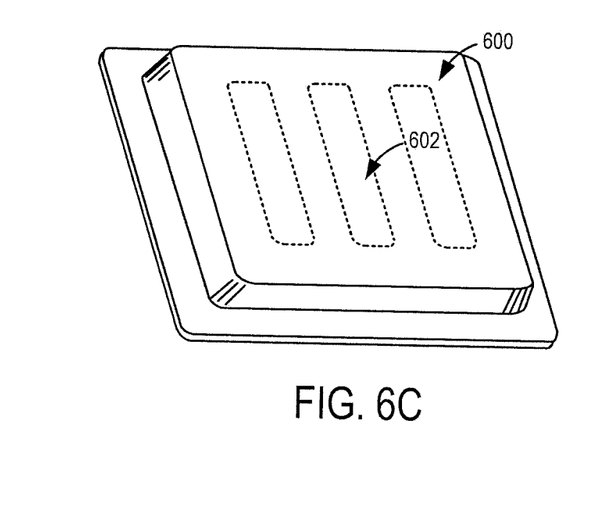
FIG. 6C is a perspective view of a volatile dispenser, in accordance with aspects of the present disclosure.
Figure 6D:
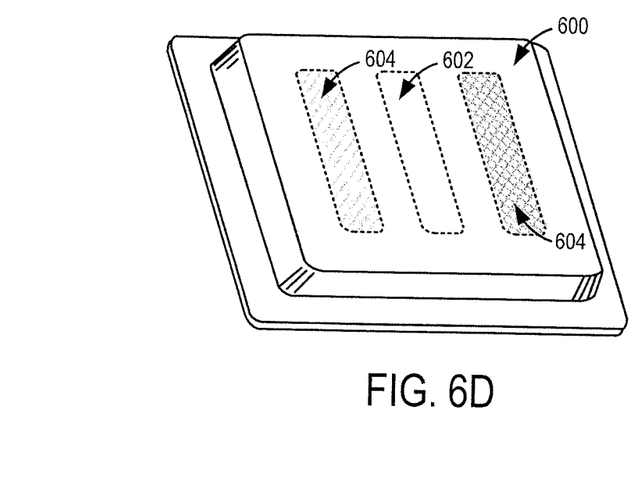
FIG. 6D is a perspective view of a volatile dispenser, in accordance with aspects of the present disclosure.

In some aspects, the material properties, including the materials and material structures, rather than thickness, can vary between the rigid portion 502 and the flexible portion 504, as illustrated in FIG. 5D. For instance, the flexible portion 504 may include materials or material structures that are different compared to those of the rigid portion 502, allowing flexure or movement of the flexible portion 504 when pressure gradients are present. However it is envisioned that any combination of thickness and material differences may be utilized, depending upon the movement and function(s) required. For instance, various materials, such as polypropylene or polyethylene, could be utilized in an injection molding process to obtain various thicknesses, as described. Also, co-molding processes could incorporate a combination of rigid and flexible materials. In addition, other manufacturing processes or treatments that allow the combination of rigid materials with flexible materials, such as laser welding, sonic welding, and other techniques, may be also possible.

Referring again to the example of FIG. 2C, changes in the amount of volatile material 134 present in the dispenser 100 and/or ambient conditions result in a depression or movement of a portion of the bottom surface 128 inward toward the sealed reservoir 132. By way of example, a displacement of the center point 140 of the bottom surface 128 could be up to about 5 mm, although other values may be possible depending on the pressure gradient present and material flexibility. Other displacements may also be possible, depending upon the dimensions, thicknesses, and material properties of the volatile dispenser 100. As shown in FIG. 2C, the membrane 122 preferably has substantially little or no flexure compared to the bottom surface 128. However, it is envisioned that the membrane 124 could have some flexure, movement, or flexible portions, depending upon the dimensions, material properties of the membrane 122, as well as present pressure differentials. For instance, an inward movement of a membrane 124 may be less than 10%, or preferably less than 1%, as compared to displacement of the center point 140, or other point or points on the bottom surface 128.

It is a discovery of the present disclosure, that volatile dispenser shape and dimension changes as a result of use, and/or intended or unintended changing environmental conditions, may be utilized to perform one or more functions in the volatile dispensing system in which it is being used. That is, rather than avoiding such shape and dimension changes via modified or reinforced designs, or supplemental features or capabilities, as attempted in previous technologies, the present approach takes advantage of these changes to achieve specific functions.

As such, volatile dispensers, in accordance with various embodiments of the present disclosure, may be engineered to include any number of flexible or movable features or elements capable of carrying out or controlling functionality of the volatile dispensing systems. For example, FIGS. 6A-6D show various embodiments, corresponding to the volatile dispenser shown in FIG. 2A, having one or more flexible portions. As described, the dispensers include rigid portions 600 that do not undergo any movement or appreciable movement. For instance, as compared to flexible portions 602 and 604 shown in FIGS. 6A-6D, any movement of the rigid portions 600, if applicable, may be less than 10%, or preferably less than 1%, as compared to movement of the flexible portions 602 and 604. As previously noted, such flexible portions may have modified thicknesses and/or modified materials or material structures, indicated in FIGS. 6A-6D by labels 602 and 604, respectively, as compared to the rigid portions 600, which do not undergo appreciable movement. It may be appreciated that the embodiments shown in FIGS. 6A-6D are mere examples, and as such, any variation in the shapes, dimensions, materials, and configurations of the rigid and flexible portions may be possible. In addition, these need not only be limited to the various surfaces or portions of the cup-shaped structure 126, as described with reference to FIGS. 2A-2C, i.e., the bottom wall 128 and the side walls 130, but may also include various surfaces or portions of the flange 120, and any combination of these.

Although the description provided herein has been directed to specific flexible portions of volatile dispensers being configured to undergo displacement, and as such provide functionality to the volatile dispenser systems in which they are used, it may be readily understood that these may also be combined with various additional control features to effect similar or other outcomes. For instance, such control features may be connectable or attachable to the volatile dispenser in a permanent or removable fashion. In addition, these may be used to enhance or reduce a displacement, or to change a directionality of motion, or to translate a linear motion to a circular motion. Further, such additional control features may be placed on sides, faces, and/or edges, singularly or in multiples or combinations as applicable in accordance with the specific application.

It is envisioned that a wide range of functionality may be implemented with the volatile dispensers disclosed herein. For example, one such function can include controlling output of the volatile material from the volatile dispensing system. In particular, as a volatile dispenser is being used, a rate or uniformity of output may change or drop with time, and/or changes in environmental conditions. As such, it may be desirable to control the output, uniformity, or directionality of the volatile material being delivered.

By way of example, FIGS. 3A-3C show a sectional view illustrating operation of an example volatile dispensing system 300 or device, in accordance with aspects of the disclosure. The dispensing system 300 may include a volatile dispenser 302, and a dispenser housing 304, as shown. The dispenser housing 304 includes primary vent openings 306 and a backup vent opening 308. It may be appreciated, that these can have any shapes and dimensions.

During an initial phase of operation, such as following installation of a new volatile dispenser 302 in the dispenser housing 304, a volatile material diffusing out of the volatile dispenser 302 would follow pathways leading out through the primary vent openings 306, as indicated by the arrows. As shown, the backup vent opening 308 would be substantially blocked by a lower portion 310 of the volatile dispenser 302, either because the volatile dispenser 302 is full, or because heat applied using a heat source (not shown) would force an expansion of the volatile dispenser 302 to close the backup vent opening 308, or a combination of both.

During an intermediate phase of operation, some of the volatile material would have diffused, thereby generating a pressure differential, as described. As a result, the lower portion 310 of the volatile dispenser 302 would have receded, or moved vertically, as shown in FIG. 3B, providing a partial pathway through the backup vent opening 308 additional to the primary vent openings 306 pathways, as indicated by the arrows. Similarly, during a final phase of operation, the lower portion 310 of the volatile dispenser 302 would have receded even further, as shown in FIG. 3C, providing additional volatile material pathways, as indicated. As may be appreciated from the above, the output or dispensing rate of the volatile dispensing system 300 could then be controlled, maintained, or enhanced, depending upon various configurations of the volatile dispenser 302.

In some envisioned variations, controlling the output of the volatile material may additionally or alternatively include mechanically operating, rotating, sliding, or moving one or more vents or vent covers or ports configured in the volatile dispensing system utilized (not shown in FIGS. 3A-3C). For example, a moving surface of a volatile dispenser could provide force or pressure on a vent cover or port, or an element logically connected thereto, to close or open various vents, or vent covers, or ports configured for adapting output or uniformity of the dispensed volatile material.

In some embodiments, environmental conditions may be taken into consideration in volatile dispenser system configurations. For instance, a volatile dispenser in accordance with various embodiments described, may be configured to respond to a hot environment, whereby the expansion of vapors within the volatile dispenser causing expansion could be used to close or minimize openings and therefore slow or moderate the interaction of volatile material being delivered. Similarly, in response to a cool environment, a volatile dispenser would be less active, and hence could be configured to provide more area or volatile material pathways.

In some embodiments, shape and dimension changes of herein provided volatile dispensers may be used to control distances in critical areas of function or fitment. For instance, shape and/or dimension changes may be used to provide a displacement or isolation from a heat source or a pressure source relative to the volatile dispenser. Also, in addition to controlling, enhancing, moderating, or stopping volatile material emission, various portions of the volatile dispensers may be configured to interact functionally with the volatile dispensing system or device in which they are being used to adapt or control alignment, retention, or adjustment. For instance, when the contents of a volatile dispenser are depleted, the volatile dispenser may be configured to be more easily removed from a volatile dispensing system or device, by allowing retraction of an interference element or feature.

Figure 4A:
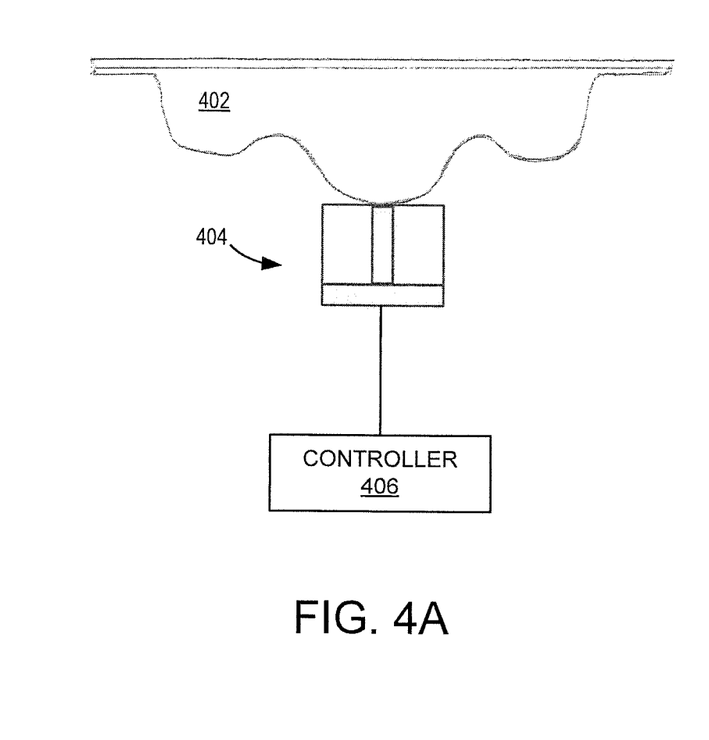
FIG. 4A is a schematic, sectional view of an example volatile dispensing system, in accordance with aspects of the present disclosure, further including a volatile dispenser similar to those shown in FIGS. 2A-2C.
Figure 4B:
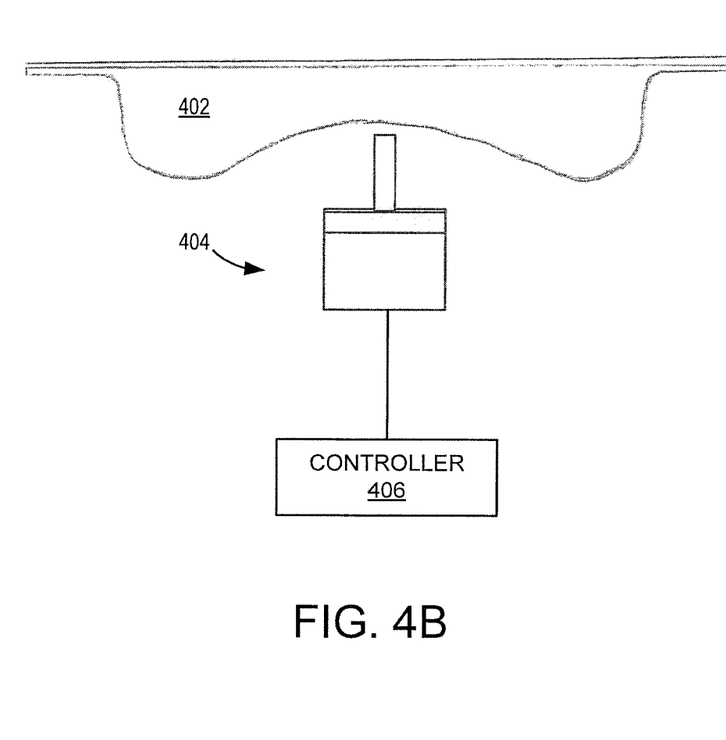
FIG. 4B is another schematic, sectional view of an example volatile dispensing system, in accordance with aspects of the present disclosure, further including a volatile dispenser similar to those shown in FIGS. 2A-2C.
Figure 7A:
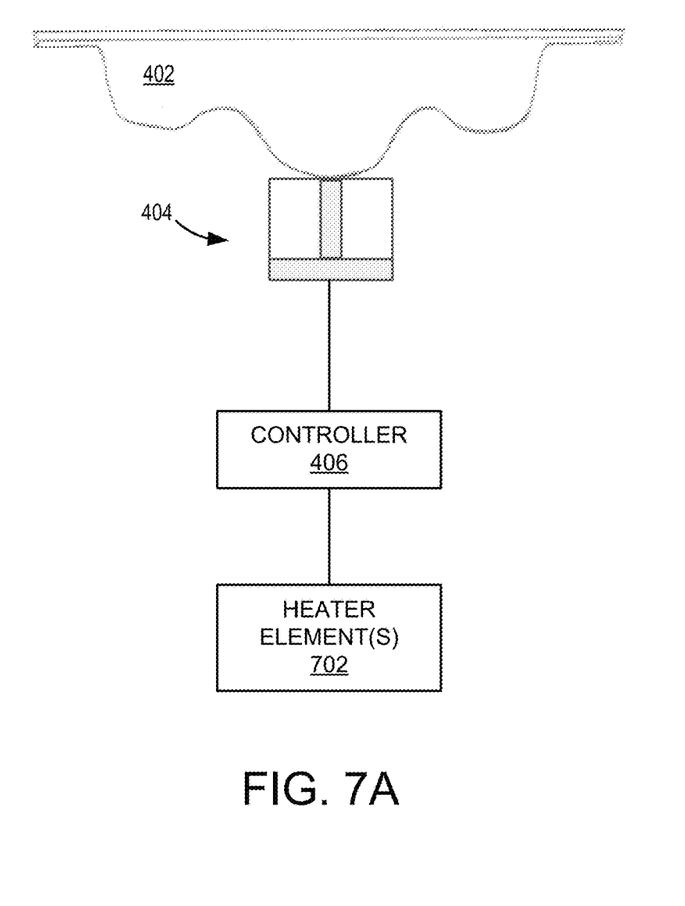
FIG. 7A is a schematic, sectional view of an expanded volatile dispensing system, in accordance with aspects of the present disclosure, further including a volatile dispenser system similar to those shown in FIGS. 2A-2C.
Figure 7B:
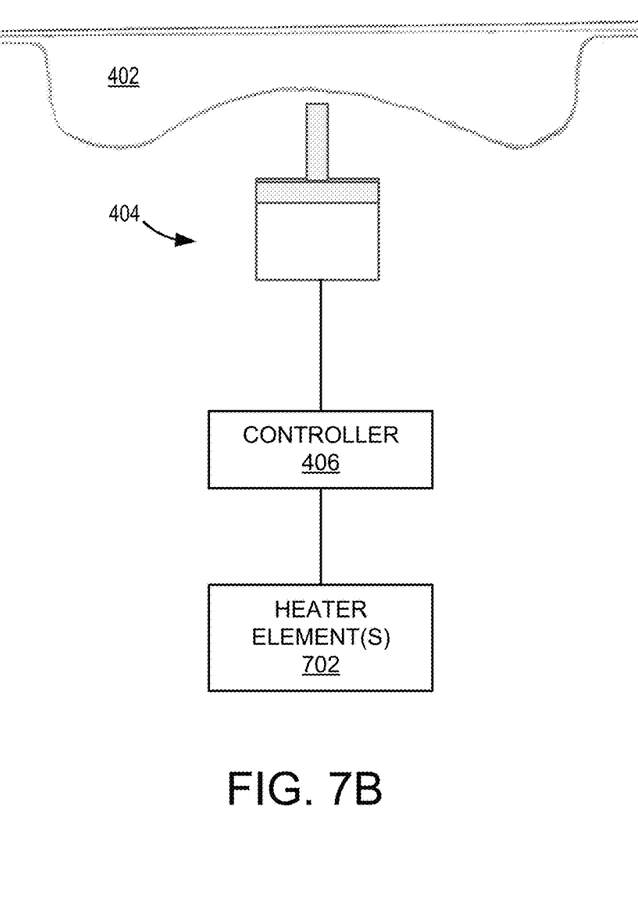
FIG. 7B is another schematic, sectional view of an example volatile dispensing system, in accordance with aspects of the present disclosure, further including a volatile dispenser similar to those shown in FIGS. 2A-2C.

In other embodiments, herein provided volatile dispensers may be configured to interact with one or more sensing devices, as well as other electronics or electrical components, such as resistors, LED's, heaters, venting systems, and so forth. For example, as shown in FIGS. 4A and 4B, a volatile dispenser 402 may be configured to interact with micro switch 404. Specifically, the micro switch 404 being in a first position (FIG. 4A), can reflect a full state of the volatile dispenser 402, while being in a second position (FIG. 4B), can reflect an empty state of the volatile dispenser 402. In some aspects, the micro switch 404 may provide a signal to the controller 406 connected thereto, as shown. Alternatively, the micro switch 404 may interrupt a signal to the controller 406. By way of example, the controller 406 may include a heat source, a pressure source, and so forth. As such, the controller 406 may affect or modify operation of the volatile dispenser based on the position of the micro switch 404. For example, the controller 406 may alter the output of the volatile material by activating or deactivating one or more heater elements configured in the volatile dispensing system utilized. As such, the controller 406 may affect or modify operation of the volatile dispenser based on the position of the micro switch 404. For example, the controller 406 may alter the output of the volatile material by activating or deactivating one or more heater elements 702 configured in the volatile dispensing system, and connected to the controller 406 as shown in FIGS. 7A and 7B.

In yet other embodiments, herein provided volatile dispensers may provide an indication to a user with respect to a state of the volatile dispenser. For example, the indication may be related to a fill level, a product life or use, a confirmation of installation, a reminder of refill, output level, output uniformity, and any other information associated with the state of the volatile dispenser. Such indication may be visual, in the form of a presence, absence, or position of a feature or element, or any other visual cue. For example, with reference to FIG. 3A, the indication may be in the form of the lower portion 310 of the volatile dispenser 302 protruding from the backup vent opening 308. In other aspects, the indication may be in the form of an LED light, a color of the volatile material, or a modified esthetic appearance.

Any of the embodiments described herein may be modified to include any of the structures or methodologies disclosed in connection with different embodiments.

INDUSTRIAL APPLICABILITY

The volatile dispensers described herein advantageously utilize dimensional and structural changes as a result of use to perform specific functions in the volatile dispensing systems in which they are being used.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A volatile dispenser for use in a volatile dispensing system, the volatile dispenser comprising:
   a blister comprising a cup-shaped structure having at least one sidewall perpendicular to a permeable membrane, a peripheral flange, and a bottom surface having a first portion and a second portion, wherein the first portion is more flexible than the second portion;
   the permeable membrane sealable to the peripheral flange and extending across the entire cup-shaped structure to form a sealed reservoir with the blister; and
   a volatile material contained within the sealed reservoir, wherein a diffusion of the volatile material through the permeable membrane generates a pressure differential inducing a movement of the first portion to perform at least one function for the volatile dispensing system, the pressure differential being between the sealed reservoir and an ambient atmosphere; and wherein only the first portion undergoes said movement as a result of the pressure differential.

2. The volatile dispenser of claim 1 further comprising a vapor impermeable laminate releasably connected to the permeable membrane and configured to substantially prevent the diffusion of the volatile material.

3. The volatile dispenser of claim 1, wherein the at least one sidewall is still perpendicular to the permeable membrane when subjected to the pressure differential.

4. The volatile dispenser of claim 1, wherein the volatile material comprises a dispensing liquid.

5. The volatile dispenser of claim 4, wherein the dispensing liquid is a diffusible fragrance.

6. The volatile dispenser of claim 4, wherein the dispensing liquid is a diffusible pest control agent.

7. The volatile dispenser of claim 1, wherein the first portion is further configured to control, based on the movement thereof, at least one of an output, a uniformity, and a directionality of the volatile material delivered by the volatile dispensing system.

8. The volatile dispenser of claim 7, wherein the first portion is further configured to control the output of the volatile material by controlling pathways for the volatile material through a dispenser housing of the volatile dispensing system.

9. The volatile dispenser of claim 7, wherein the first portion is further configured to control the output of the volatile material by controlling flow of the volatile material through one or more vent openings in the volatile dispensing system.

10. The volatile dispenser of claim 7, wherein the first portion is further configured to control the output of the volatile material by controlling operation of one or more heater elements in the volatile dispensing system.

11. The volatile dispenser of claim 1, wherein the at least one function includes interacting with a sensing device.

12. The volatile dispenser of claim 1, wherein the at least one function includes providing an indication with respect to a state of the volatile dispenser.

13. The volatile dispenser of claim 1, wherein a thickness of first portion has a thickness that is less than a thickness of the second portion.

14. The volatile dispenser of claim 1, wherein the first portion includes a material that is different compared to the second portion.

15. A volatile dispenser for use in a volatile dispensing system, the volatile dispenser comprising:
    a blister comprising a cup-shaped structure formed from a single sheet, the cup-shaped structure having at least one sidewall and a bottom surface having a first portion and a second portion, wherein the first portion is more flexible than the second portion;
    a permeable membrane sealable to the cup-shaped structure and configured to form a sealed reservoir with the blister; and
    a volatile material contained within the sealed reservoir, wherein a diffusion of the volatile material through the permeable membrane generates a pressure differential inducing a movement of the first portion to perform at least one function for the volatile dispensing system, the pressure differential being between the sealed reservoir and an ambient atmosphere; and wherein only the first portion undergoes said movement as a result of the pressure differential.

16. The volatile dispenser of claim 15, wherein a thickness of the first portion has a thickness that is less than a thickness of the second portion.

17. The volatile dispenser of claim 16, wherein the thickness of the first portion is between 20% to 50% of the thickness of the second portion.

18. The volatile dispenser of claim 15, wherein the first portion includes a material that is different compared to the second portion.

\* \* \* \* \*